(12) United States Patent
Kiessling et al.

(10) Patent No.: US 9,841,355 B2
(45) Date of Patent: Dec. 12, 2017

(54) METHOD FOR OPERATING AN IGNITION DEVICE

(71) Applicant: PRUEFEX engineering e motion gmbh & co.kg, Cadolzburg (DE)

(72) Inventors: Leo Kiessling, Cadolzburg (DE); Thomas Fruehwald, Nuremberg (DE)

(73) Assignee: PRUEFREX engineering e motion GmbH & Co. KG, Cadolzburg (DE)

( * ) Notice: Subject to any disclaimer, the term of this patent is extended or adjusted under 35 U.S.C. 154(b) by 206 days.

(21) Appl. No.: 14/565,973

(22) Filed: Dec. 10, 2014

(65) Prior Publication Data

US 2015/0160095 A1  Jun. 11, 2015

(30) Foreign Application Priority Data

Dec. 10, 2013 (DE) .................. 10 2013 020 739

(51) Int. Cl.
| | |
|---|---|
| G01M 15/04 | (2006.01) |
| G01N 27/00 | (2006.01) |
| F02D 41/00 | (2006.01) |
| F02P 1/08 | (2006.01) |
| F02P 3/08 | (2006.01) |
| F02P 7/067 | (2006.01) |
| F02P 11/00 | (2006.01) |
| F02P 5/15 | (2006.01) |

(52) U.S. Cl.
CPC ....... *G01M 15/042* (2013.01); *F02D 41/0097* (2013.01); *F02P 1/086* (2013.01); *F02P 3/0861* (2013.01); *F02P 7/067* (2013.01); *F02P 11/00* (2013.01); *G01N 27/00* (2013.01); *F02D 2400/06* (2013.01); *F02P 5/1502* (2013.01)

(58) Field of Classification Search
CPC . F23Q 23/00; F02P 17/00; F02P 17/12; F02P 2017/003; F02P 1/00; F02P 3/06; F02P 5/15; F02P 17/02; G01R 31/006; F02N 11/06; H02K 21/00; G01M 15/042; G01M 15/04; G01N 27/00; Y02T 10/40; Y02T 10/128; F02D 2400/06; F02D 41/009; F02D 41/0097; F02D 37/02; F02D 2200/021; F02D 2250/12; F02B 2075/025; F02B 2075/027
USPC ................................. 73/0.62–0.67
See application file for complete search history.

(56) References Cited

U.S. PATENT DOCUMENTS

| 8,032,292 B2 | 10/2011 | Kiessling et al. | |
|---|---|---|---|
| 2003/0011397 A1* | 1/2003 | Briendl .................. | H02K 15/16 702/182 |

(Continued)

FOREIGN PATENT DOCUMENTS

| DE | 102 01 422 A1 | 3/2003 |
|---|---|---|
| DE | 102 14 524 B4 | 6/2006 |
| EP | 2 020 502 A1 | 2/2009 |

*Primary Examiner* — Hezron E Williams
*Assistant Examiner* — Timothy Graves
(74) *Attorney, Agent, or Firm* — Muncy, Geissler, Olds & Lowe, P.C.

(57) ABSTRACT

A method for operating an ignition device for an internal combustion engine, in which via a rotating magnetic pole wheel a voltage signal with a number of positive and negative half-waves is produced in at least one coil arrangement that is located on a core leg of an iron core during each rotation of the magnetic pole wheel, wherein the voltage signal is used to determine the gap width of the air gap between the magnetic pole wheel and the core leg.

10 Claims, 4 Drawing Sheets

(56) References Cited

U.S. PATENT DOCUMENTS

| | | | |
|---|---|---|---|
| 2003/0056755 A1* | 3/2003 | Kiessling | F02D 37/02 123/406.24 |
| 2006/0169249 A1* | 8/2006 | Shimoyama | F02P 1/086 123/406.53 |
| 2009/0084368 A1* | 4/2009 | Kiessling | F02P 1/086 123/601 |

* cited by examiner

METHOD FOR OPERATING AN IGNITION DEVICE

This nonprovisional application claims priority to German Patent Application No. DE 10 2013 020 739.8, which was filed in Germany on Dec. 10, 2013, and which is herein incorporated by reference.

BACKGROUND OF THE INVENTION

Field of the Invention

The present invention relates to a method for operating an ignition device, in particular a magneto ignition system or device, for an internal combustion engine. It also concerns an ignition device operating in accordance with said method.

Description of the Background Art

Ignition devices of this nature are typically used in hand-operated tools powered by an internal combustion engine. To determine speed, an electronics unit analyzes at least one voltage signal with positive and negative half-waves produced by generator action, which is to say induced by means of an electromagnet (magnet generator). With the customary construction of such an ignition device having a magnetic pole wheel coupled to the internal combustion engine, for example to its crankshaft, and having a typically U-shaped iron core with a coil (trigger, charging, and/or ignition coil) located on at least one of the core legs thereof, the rotation of the magnetic pole wheel equipped with permanent magnets results in an induced voltage in the relevant coil, wherein the coil voltage has negative and positive half-waves. The electronics unit infers the speed and, in particular, also the direction of rotation of the magnetic pole wheel from the time-dependent and/or rotation-angle-dependent sequence of positive and negative half-waves. Active components, in particular transistors, and a microprocessor are used to determine the speed and/or angular positions, as well for any signal processing.

It is known from DE 102 01 422 A1 that an air gap between the magnetic pole wheel and the core leg that varies or is subject to dispersion can affect the voltage amplitude of the coil signal, in particular of the trigger coil, in exactly the same way as varying strength of the pole wheel magnet, which in turn can cause an incorrect determination of angular position. In order to ascertain a correction factor, it is proposed there to compare the angular position determined through a positive or negative threshold exceedance with a mean angular position that can be ascertained from the typical AC voltage pattern of the coil signal or trigger signal. Since there is no load dependence at the time of a threshold analysis, it is assumed there that the two angular positions ascertained from the mean value and from the threshold analysis would normally have to be equal. A change in an air gap and/or magnet strength can then be inferred from a deviation.

SUMMARY OF THE INVENTION

It is therefore an object of the present invention to provide an especially suitable method for operating an ignition device, wherein a maximally reliable air gap determination or at least an air gap estimation should be made possible. An additional object is to specify an ignition device that operates according to this method.

A voltage signal that can be taken off at a charging coil, for example, but preferably at the trigger coil in particular, in particular a maximum voltage value or peak voltage value of a specific positive half-wave of the voltage signal (trigger signal), can be used to determine the air gap, which is to say the gap width thereof or the clear opening between the applicable core leg of the iron core and the magnetic pole wheel.

The position of the core legs relative to the magnetic pole wheel, and thus a tipping or tilting of the iron core, can be detected from a deviation of the air gap ascertained from two voltage signals from coils located on the two adjacent core legs of the iron core.

The invention is based on the finding that the signal strength of the voltage signal of the coil used for this purpose, in particular including the height or amplitude of the trigger voltage, is speed-dependent, and rises essentially linearly with speed. In this context, a discontinuity in the rise of the lines arises in the region of approximately 4,000 revolutions that can be attributed to the shut-off of what is called the high-voltage switch and of the energy thus supplied to the ignition capacitor. In other words, the speed-dependent voltage height of the coil signals changes as a function of the size of the air gap in a manner that is characteristic and can be described by a function. For the purpose of ascertaining speed and/or detecting angular position, threshold values can be used, which is to say the positive or negative exceedance thereof by specific half-waves of the coil signals or voltage signals.

The air gap dependence here is reflected largely in different slopes of the voltage/speed curves. The speed-dependent slope rises more sharply for smaller air gaps than for comparatively large air gaps. This in turn results in a functional relationship from which it is possible to determine that the voltage height of the coil signals, which is to say the amplitude of a specific half-wave in particular, does not decrease linearly with increasing air gap. Instead, the curve of the function corresponds to a $1/x^n$ function.

According to an embodiment, a voltage value of at least one of the positive half-waves of the voltage signal is measured as a function of speed and is used to determine the gap width of the air gap. In particular, in this embodiment the peak voltage value of the same periodically occurring positive half-waves of the voltage signal is measured and is used to determine the gap width of the air gap.

In an embodiment, the measured voltage value or peak voltage value is compared to stored value pairs consisting of speed and voltage value or peak voltage value for different gap widths. When the voltage or peak voltage values agree, the gap width of the air gap is determined. In this design, the gap width of the air gap is determined in particular based on a number of characteristic curves stored for different gap widths, from which the voltage value or peak voltage value measured for the current speed or a specific speed is determined.

The different gap widths are each measured for different speeds and the associated voltage values (peak value of a specific positive half-wave) of the coil signal (trigger signal). These pairs of values are stored. From these value pairs, the controller ascertains the slope of the corresponding function curve. The gap width of the air gap is determined from this based on a stored table, family of lines, or family of characteristic curves. In other words, the voltage value or peak voltage value measured at the current speed or a specific speed is compared with characteristic curves, value pairs, or a family of lines stored for different gap widths (air gap values), and the gap width of the air gap is determined from the characteristic curve identified in the process.

In an embodiment, the controller, for example a microprocessor, also extracts from a stored table a correction value associated with the applicable air gap or its gap width, which correction value depends on operational parameters, such as, in particular, the temperature or a (current) segment speed of the magnetic pole wheel. In other words, the ascertained value of the air gap, i.e., its gap width, is weighted with at least one correction value identified for an operational parameter. In particular, the temperature of the ignition device, preferably its control unit, and/or a segment speed is measured as an operational parameter. The ascertained gap width of the air gap is then weighted with a correction value associated with this parameter.

The ignition device comprises a magnetic pole wheel and at least one coil (coil arrangement) that is located on a core leg of an iron core, and that, as a result of rotation of the magnetic pole wheel, generates a first voltage signal—or two voltage signals in the case of two coil arrangements (coils) on two core legs spaced apart from one another—with positive and negative half-waves, and also comprises a control or regulating device (microprocessor) that is configured to carry out the method according to the invention.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION

Figure 1:
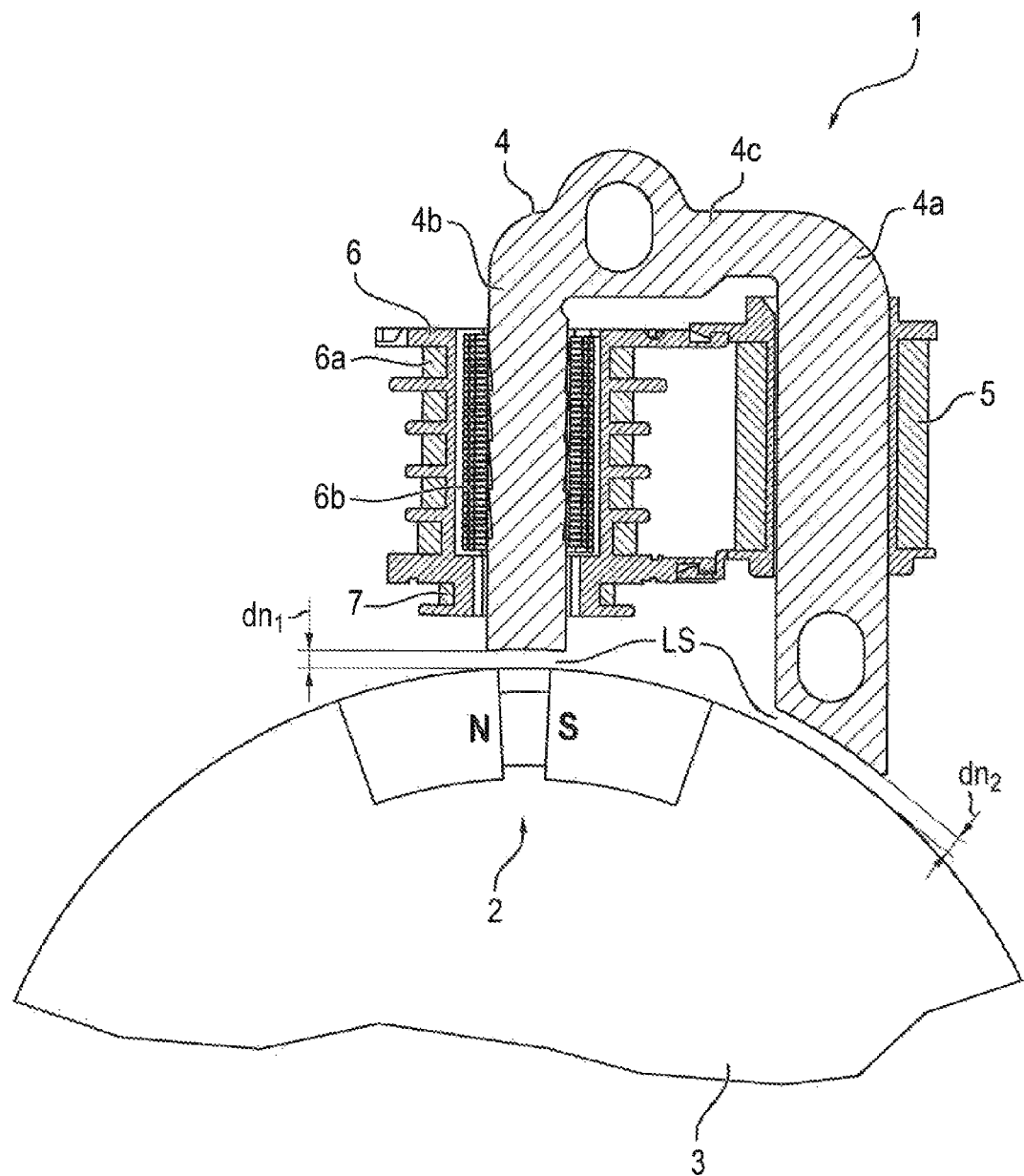
FIG. 1 is a schematic sectional view of an ignition device with a U-shaped iron core with coils located thereon and also with a magnetic pole wheel arranged to form an air gap to the iron core.

FIG. 1 schematically shows an ignition device 1 with a pole wheel (magnetic pole wheel) 3 having a magnet 2 with a north and a south pole (N, S), which pole wheel rotates synchronously with an internal combustion engine that is not shown in detail. The permanent magnet 2, or for example two permanent magnets 2 (FIG. 2) is/are located in a circle sector or circle segment of the circular magnetic pole wheel 3. The ignition device 1 also has a stationary U-shaped iron core 4 with a first core leg 4a and with a second core leg 4b. The two core legs spaced apart from one another are connected to one another by a middle part 4c.

An air gap LS is formed between each of the free ends of the core legs 4a, 4b and the magnetic pole wheel 3. The gap width ($d_n$) of the air gap LS between the magnetic pole wheel 3 on one side and the core leg 4b or 4a on the other side is labeled $d_{n1}$ or $d_{n2}$, respectively. The distance or the arrangement of the core legs 4a, 4b is matched to the dimensions or to the configuration of the magnet 2, wherein the magnetic flux is closed through the iron core 4.

Located on the core leg 4a is a charging coil 5, in whose coil winding a current is induced due to the magnetic flux, wherein a corresponding voltage curve or signal curve ($U_n$) can be taken off at the coil winding or its winding ends as a first voltage signal $U_{LS}$. In an analogous manner, an ignition transformer 6 with a primary winding 6a and a secondary winding 6b, frequently also called an ignition coil, is located on the adjacent core leg 4b, wherein a current is likewise induced in the primary winding 6a. Also located on this second core leg 4b is a trigger coil 7 that supplies a voltage curve or signal curve ($U_n$) as a second voltage signal $U_{TS}$. The second voltage signal $U_n$ can also be supplied by the primary winding 6a of the ignition transformer 6. In addition, a suitable voltage signal $U_n$ can be taken from an ignition or high voltage cable (not shown) to a spark plug (FIG. 2) based on the coupling between the primary and secondary windings (using the step-up ratio to the secondary coil 6b).

Figure 2:
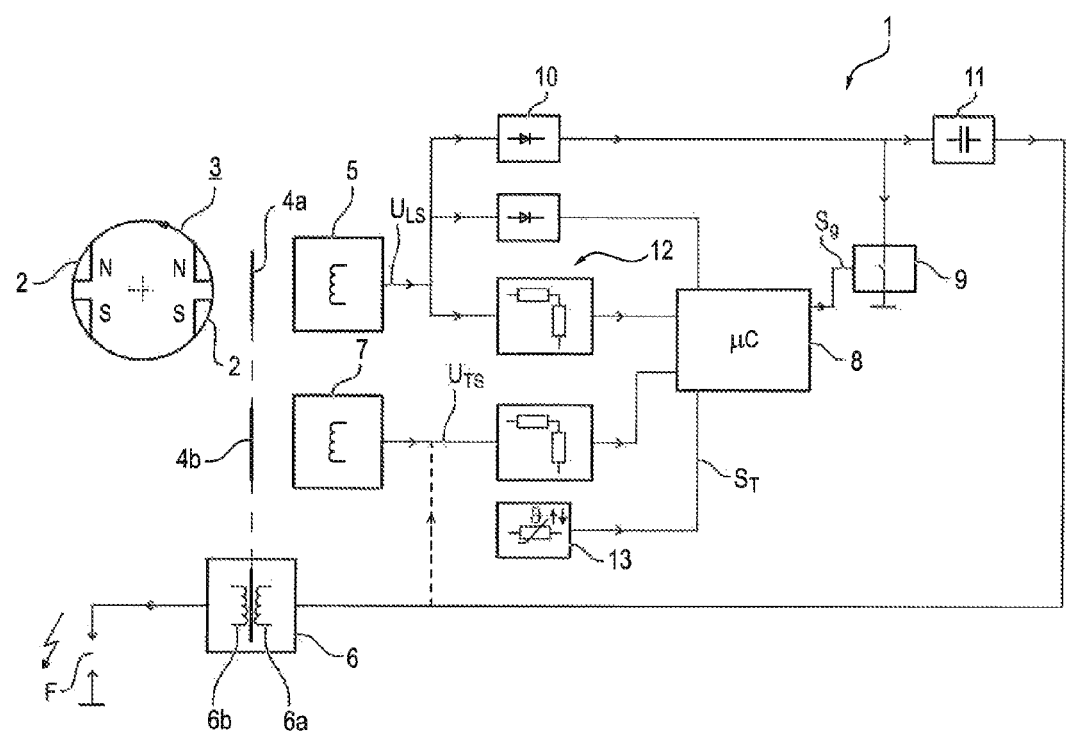
FIG. 2 is a block diagram of the ignition device with a control and/or analysis or computing device (microprocessor) for determining the air gap, and with a charging coil, a trigger coil, and a pulse transformer.

FIG. 2 shows the ignition device 1 and its circuit components in a block diagram. The ignition device 1 comprises a control and/or regulating device 8 in the form of a microcontroller or microprocessor that is connected at its output side to the control side of an ignition switch 9 in the form of a semiconductor switch, for example a TRIAC, which in turn is connected to ground.

The charging coil 5 is connected to an ignition capacitor 11 by a rectifier 10 in the form of, for example, a diode, or a half-bridge or full-bridge rectifier, which in turn is connected to the primary winding 6a of the ignition transformer 6. On the secondary side, the secondary winding 6b of the ignition transformer 6 is routed to a terminal (not specifically labeled) of the ignition device 1, to which the spark plug for generating an ignition spark F for the internal combustion engine is or can be connected, for example.

The ignition switch 9 is closed as a result of an ignition or drive signal $S_g$ produced (generated) by the microcontroller 8 at a specific, adjustable ignition time. In consequence, the ignition capacitor 11 is discharged through the primary coil 6a of the ignition transformer 6, which results in a corresponding, sufficient high voltage at the secondary side for triggering the ignition spark F on account of the turns ratio of the primary coil 6a to the secondary coil 6b.

A current source / voltage source 12 (power supply) is supplied with energy from the charging coil 5 and/or from the trigger coil 7 to provide power and the supply voltage for the microprocessor 8. The voltage signal $Up_{LS}$ of the charging coil 5 and the voltage signal $U_{TS}$ of the trigger coil 7 or of the ignition transformer 6 are supplied to the input side of the microprocessor 8. The microprocessor 8 additionally receives a temperature signal $S_T$ from a temperature sensor 13 that measures the temperature or heat generation of the ignition device 1 and/or of the microprocessor 8.

Figure 3:
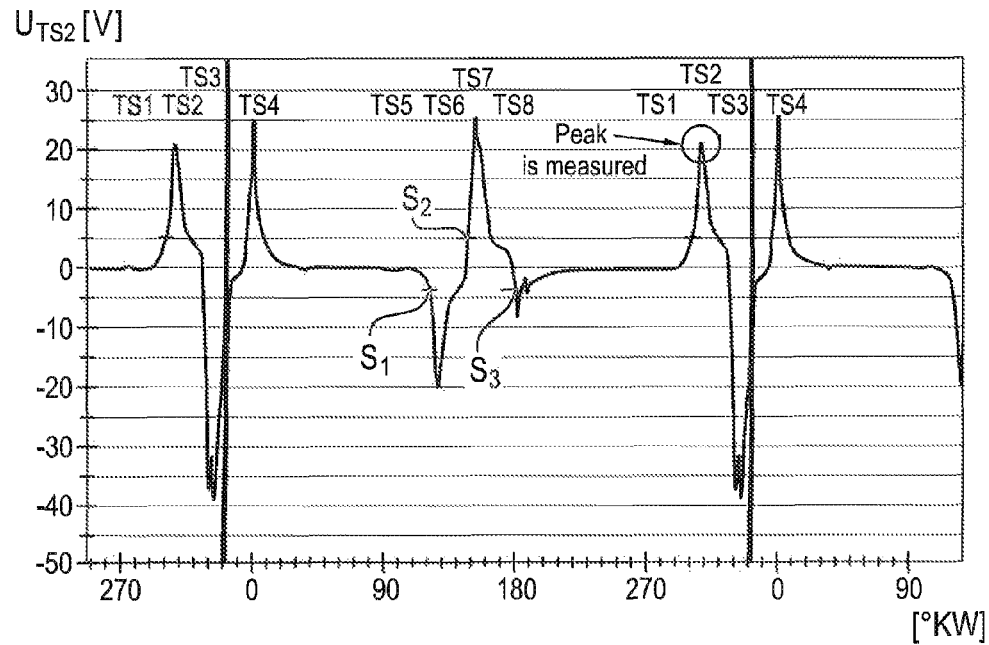
FIG. 3 is a voltage/rotational angle diagram of the voltage signal with characteristic positive and negative half-waves generated by one of the coils (trigger coil) in the course of operation of the ignition device as a generator.

FIG. 3 shows the behavior over time of the voltage signal $U_{TS}$ of the trigger coil 7. The time behavior corresponds to the counterclockwise direction of rotation (forward direction) drawn in FIG. 2 of the magnetic pole wheel 3. The curve also corresponds to the time behavior of the voltage signal $U_{LS}$ of the charging coil 5 and of the ignition transformer 6 or its primary winding 6a.

As is evident, the voltage signal $U_{TS}$ has a series of negative and positive half-waves. The maxima and minima of the voltage signal $U_{TS}$ correlate with specific angular positions (in specific pole wheel segments) of the magnetic pole wheel 3, wherein the zero crossing between the two pronounced positive and negative half-waves whose voltage peaks (peak values) are labeled in FIG. 3 with TS2 to TS3 is associated with the angular position between the magnetic poles (N, S) of one of the magnets 2. The other magnet 2 generates the half-waves (minima and maxima) of the voltage signal $U_{TS}$ labeled TS6 to TS8. The half-waves labeled TS6 and TS8 are used for determining (ascertaining) the speed in that a time-dependent positive exceedance and/or negative exceedance of specific threshold values $S_{1,2,3}$ is detected, and the current speed x is ascertained therefrom.

The curve shown in FIG. 3 of the voltage signal $U_{TS}$, also referred to as the trigger voltage, was recorded at a gap width $d_n=0.3$ nm of the air gap LS and a speed $x=6000$ rpm$^{-1}$ of the crankshaft of the internal combustion engine. In the discussion that follows, it is assumed that the voltage value or peak (peak value) of the positive half-wave labeled TS2 is measured as a function of speed and is used to determine the gap width $d_n$ of the air gap LS.

Figure 4:
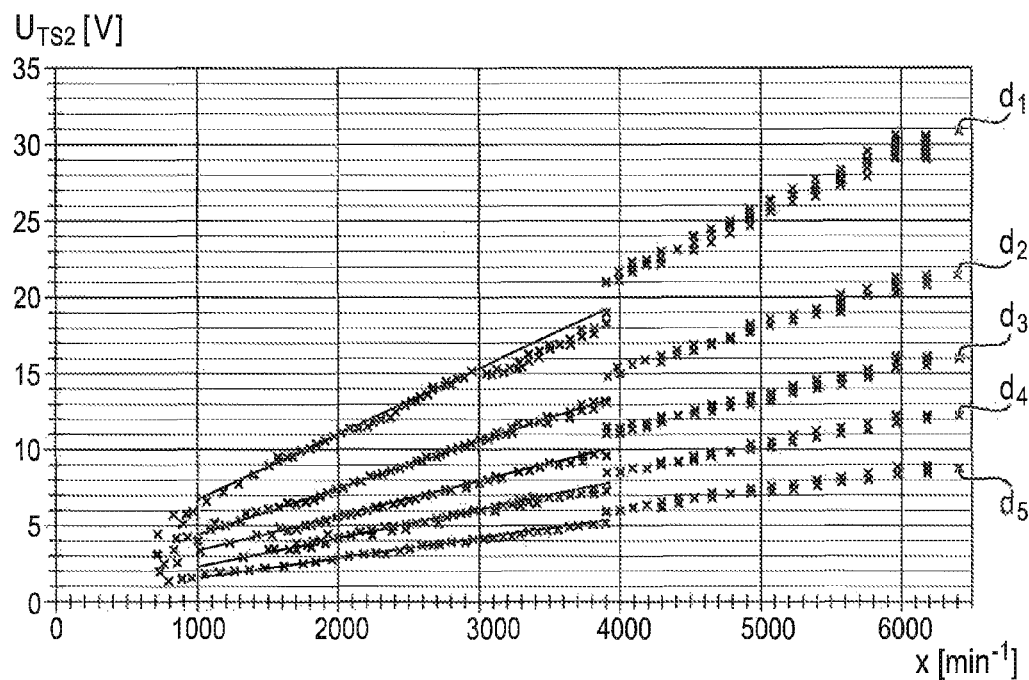
FIG. 4 is a voltage/speed diagram of a family of lines with discrete value pairs for different gap widths of the air gap.

The family of lines or characteristic curves shown in FIG. 4 contains peak voltage values $U_{TS2}$ of the voltage signal $U_{TS}$ recorded as a function of speed for different gap widths $d_1$ to $d_5$. It is evident that, with increasing speed x, the voltage value (peak at TS2), which is also referred to below as the peak value, initially increases approximately linearly. The discontinuity in the course of the lines at approximately 4000 revolutions per minute (min$^{-1}$) can be attributed to the so-called high-voltage switch. The high-voltage switch region below this speed ($x\approx 4000$ min$^{-1}$) is marked with approximation lines for the value pairs (x, $U_{TS2}$).

The family of characteristic curves or family of lines shown was recorded at a temperature of 20° C. and a spark path of 2 kV. The gap width $d_n$ increases from $d_1$ to $d_5$ by a factor of approximately two (2) in each case. An air gap width of $d_1=0.1$ mm is associated with the line labeled $d_1$, while a gap width of $d_5=2.0$ mm is associated with the line labeled $d_5$. The gap widths of the remaining lines are $d_2=0.3$ mm, $d_3=0.5$ mm and $d_4=1.0$ mm.

According to the relationship $y=y_0+m\cdot x$, at the speed X the lines shown approximate the peak value of the corresponding positive half-wave (TS2) of the voltage signal $U_{TS}$ with specific parameters $y_0$ (in V) for the different gap widths $d_n$. The slope m (in mV/rpm) increases towards smaller gap widths $d_n$—as do the values $y_0$.

Figure 5:
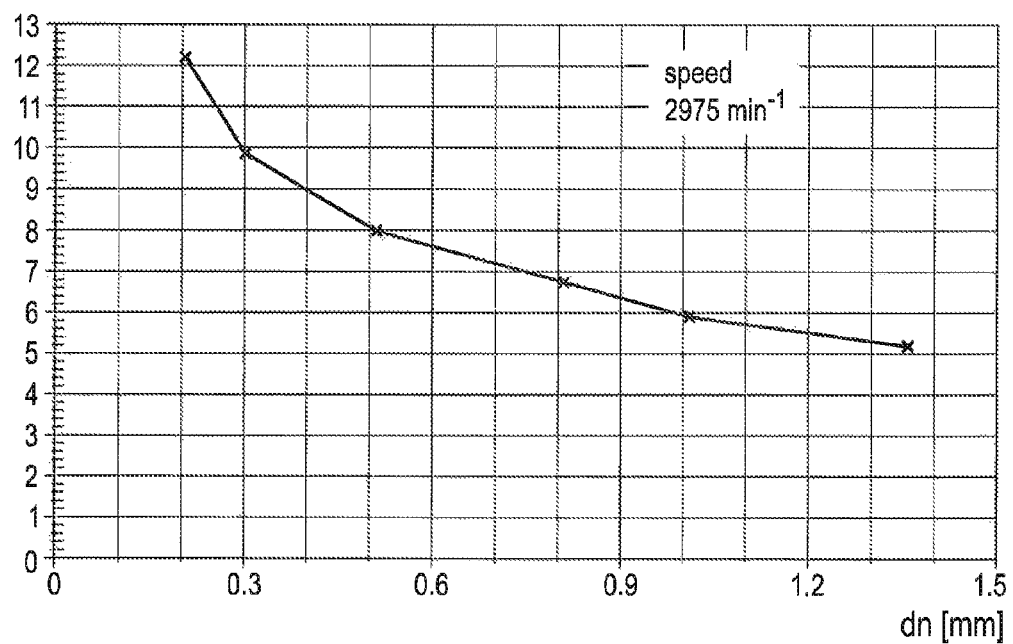
FIG. 5 is a voltage/gap width diagram of a function curve associated with a specific speed.

FIG. 5 shows the function curve approximated through measured value pairs ($d_n$, $U_{TS2}$) at a specific speed x, where $x=2975$ min$^{-1}$. The approximated function corresponds to the relationship $a+b\cdot x^{-1}-c\cdot x^{-2}+d\cdot x^{-3}-e\cdot x^{-4}$.

The microprocessor 8, or its algorithm, ascertains the current speed x and associates therewith the peak value $U_{TS2}$ measured in each case. On the basis of this value pair (x, $U_{s2}$), the microprocessor 8 or its algorithm identifies the associated gap width $d_n$ of the air gap LS from the characteristic curves or from the family of lines shown in FIG. 4.

Once the voltage signal $U_{LS}$ of the charging coil 5 and also the voltage signal $U_{TS}$ of the trigger coil 7 have both been measured and analyzed, then the gap widths $d_{n1}$, $d_{n2}$ of the two core legs 4b and 4a relative to the magnetic pole wheel 3 can be ascertained in the stated manner. A tipping or tilting of the iron core 4 can be inferred from these values of the gap widths $d_{n1}$ and $d_{n2}$, and in particular from their deviation from one another.

The gap width $d_n$ identified in each case is preferably corrected as a function of temperature. The sensor-measured temperature signal $S_T$ is used for this purpose, and is taken into consideration by software means by way of the microprocessor 8. Moreover, in suitable fashion the measured speed x is corrected relative to the segment speed by a specific value, for example 200 rpm, and weighted correspondingly for this purpose.

With regard to the sequence when correction values are taken into consideration, first the peak value $U_{TS2}$ is ascertained, preferably by means of a peak value search. This voltage value or peak value $U_{TS2}$ is corrected on the basis of the temperature $S_T$ measured in the control unit (ignition device 1, microprocessor 8). In addition, the current segment speed is provided with a correction based on the braking of the compression. Using this corrected speed value x and the slope m from the stored family of lines shown in FIG. 4, the expected voltage value $U_{TS2}$ at the associated stored gap width $d_n$ of the air gap LS is identified. This expected voltage value $U_{TS2}$ is compared with the measured voltage value $U_{TS2}$. The current, actual gap width $d_n$ of the air gap LS is determined from an agreement between these two voltage values $U_{TS2}$ (measured and stored).

The ascertained gap width $d_n$ of the air gap LS is used in particular to reliably detect the crankshaft angle, for example at large gap widths $d_n$, and if applicable to suppress a spark emission. Moreover, the voltage thresholds of the voltage signal $U_{TS}$ can be chosen optimally with respect to the signal-to-noise ratio. In addition, the ascertainment of the actual gap width $d_n$ of the air gap LS can be utilized for diagnostic purposes. Furthermore, it is possible to recognize a tilting due to different gap widths $d_{n1}$, $d_{n2}$ of the iron core 4.

The invention being thus described, it will be obvious that the same may be varied in many ways. Such variations are not to be regarded as a departure from the spirit and scope of the invention, and all such modifications as would be obvious to one skilled in the art are to be included within the scope of the following claims.

What is claimed is:

1. A method for determining a gap width of an ignition device air gap for an internal combustion engine that includes at least one coil arrangement, which is arranged on a core leg of a U-shaped iron core, which faces only a partial section of a circular sector of a magnetic pole wheel, the method comprising:

producing a voltage signal with a number of positive and negative half-waves during each rotation of the magnetic pole wheel in at least one coil arrangement, which is arranged on the core leg of the U-shaped iron core, which faces only the partial section of the circular section of the magnetic pole wheel;

measuring a voltage value or a peak voltage value of at least one of the positive half-waves of the voltage signal;

determining a rotational speed of the magnetic pole wheel from the measured voltage value or peak voltage value;

determining a gap width of an air gap between the magnetic pole wheel and the core leg based on the determined rotational speed of the magnetic pole wheel and the voltage signal.

2. The method according to claim 1, wherein a peak voltage value of a same periodically occurring positive half-waves of the voltage signal is measured as a function of speed and is used to determine the gap width of the air gap.

3. The method according to claim 1, wherein the voltage value or peak voltage value measured as a function of speed is compared with voltage values or peak voltage values stored as a function of speed for different gap widths of the air gap, and wherein the gap width of the air gap is determined when the voltage values or peak voltage values match.

4. The method according to claim 1, wherein the gap width of the air gap is determined from the voltage value or peak voltage value measured at a current speed or a specific speed based on a number of functions stored for different gap width.

5. The method according to claim 1, wherein the voltage value or peak voltage value measured at a current speed or a specific speed is compared with characteristic curves stored for different gap widths according to the relationship $$y(TS2)=y0+m \cdot x$$

and, wherein the gap width of the air gap is determined from a characteristic curve identified in so doing, where y0 [V] is an initial or correction value, x [rpm] is a speed, and m [mV/rpm] is a slope of the characteristic curve or line associated with the gap width.

6. The method according to claim 1, wherein an ascertained gap width of the air gap is weighted with at least one correction value ascertained for an operational parameter.

7. The method according to claim 1, wherein the temperature of the ignition device or its control unit, and/or a segment speed is measured as the operational parameter, and the ascertained gap width of the air gap is weighted with a correction value associated with this parameter.

8. A method for operating an ignition device for an internal combustion engine that includes at least two coil arrangements, which are arranged on mutually spaced first and second core legs of a U-shaped iron core, which faces only a partial section of a circular sector of a magnetic pole wheel, the method comprising:

producing a first voltage signal of a first coil arrangement associated with the first core leg and the second voltage signal of a second coil arrangement associated with the second core leg, each with a number of positive and negative half-waves during each rotation of the magnetic pole wheel, measuring a first voltage value or a first peak voltage value of at least one of the positive half-waves of the first voltage signal, and measuring a second voltage value or a second peak voltage value of at least one of the positive half-waves of the second voltage signal;

determining a rotational speed of the magnetic pole wheel from the measured first or second voltage value or first or second peak voltage value;

determining first and second gap widths of an air gap between the magnetic pole wheel and the first and second core legs, a position of the first and second core legs and/or of the U-shaped iron core relative to the magnetic pole wheel; and detecting tipping or tilting of the U-shaped iron core relative to the magnetic pole wheel from a deviation of the first and second gap widths.

9. An ignition device for an internal combustion engine, the ignition device comprising:

a magnetic pole wheel; and at least one coil arrangement that is arranged on a core leg of a U-shaped iron core and that, as a result of rotation of the magnetic pole wheel, generates a voltage signal with a number of positive and negative half-waves during each rotation of the magnetic pole wheel; and a control or regulating device that is configured to carry out the method according to claim 1.

10. An ignition device for an internal combustion engine, the ignition device comprising:

a magnetic pole wheel; and at least two coil arrangements that are arranged on mutually spaced first and second core legs of a U-shaped iron core and that, as a result of rotation of the magnetic pole wheel, generates first and second voltage signals, each with a number of positive and negative half-waves during each rotation of the magnetic pole wheel; and a control or regulating device that is configured to carry out the method according to claim 8.

* * * * *